US011484363B2

(12) United States Patent
Schneider et al.

(10) Patent No.: US 11,484,363 B2
(45) Date of Patent: *Nov. 1, 2022

(54) SYSTEM AND METHOD FOR DETERMINING THE POSITION AND ORIENTATION OF A TOOL TIP RELATIVE TO EYE TISSUE OF INTEREST

(71) Applicant: Elbit Systems Ltd., Haifa (IL)

(72) Inventors: Ron Schneider, Haifa (IL); Abraham Zeitouny, Haifa (IL); Einav Namer Yelin, Haifa (IL); Rani Ben-Yishai, Tel Aviv-Jaffa (IL)

(73) Assignee: Elbit Systems Ltd., Haifa (IL)

( * ) Notice: Subject to any disclaimer, the term of this patent is extended or adjusted under 35 U.S.C. 154(b) by 518 days.

This patent is subject to a terminal disclaimer.

(21) Appl. No.: 16/516,647

(22) Filed: Jul. 19, 2019

(65) Prior Publication Data

US 2019/0336222 A1 Nov. 7, 2019

Related U.S. Application Data

(63) Continuation-in-part of application No. 16/066,480, filed as application No. PCT/IL2016/051370 on Dec. 22, 2016, now Pat. No. 10,433,916.

(30) Foreign Application Priority Data

Dec. 28, 2015 (IL) .......................... 243384

(51) Int. Cl.
*A61B 5/00* (2006.01)
*A61B 34/10* (2016.01)
(Continued)

(52) U.S. Cl.
CPC .............. *A61B 34/10* (2016.02); *A61B 34/20* (2016.02); *A61B 90/39* (2016.02);
(Continued)

(58) Field of Classification Search
IPC ................. A61B 5/10,5/20, 5/39, 5/102, 5/105, 5/2065
See application file for complete search history.

(56) References Cited

U.S. PATENT DOCUMENTS 8,945,140 B2  2/2015 Hubschman et al.
2007/0171369 A1* 7/2007 Grundig ............. G06K 9/00604
351/210

(Continued)

FOREIGN PATENT DOCUMENTS

CN 1379647 A 11/2002
CN 1505491 A 6/2004
(Continued)

OTHER PUBLICATIONS

Office Action dated Dec. 2, 2019, for Chinese Application No. 2016-8008-12162.

(Continued)

*Primary Examiner* — Joel F Brutus
(74) *Attorney, Agent, or Firm* — Brown Rudnick LLP (57) ABSTRACT

System for determining a position of a tool-point-of-interest of a tool, relative to an eye-tissue-of-interest, which includes and imager a tool-tracker and a processor. The imager acquires an image of a tissue-reference-marker. The tool-tracker determines information relating to the P&O of the tool in a reference-coordinate-system. The imager and the tool-tracker are in registration with the reference-coordinate-system. The processor determines the position of the tissue-reference-marker in the reference-coordinate-system, according to the acquired image of the tissue-reference-marker. The processor determines the P&O of the eye-tissue-of-interest in the reference-coordinate-system according to at least the position of the tissue-reference-marker and a relative position between the tissue-reference-marker and the eye-tissue-of-interest. The relative position is pre-deter- (Continued)

mined from a stored-3D-model. The processor determines the position of a tool-point-of-interest in the reference-coordinate-system from the P&O of the tool in the reference-coordinate-system. The processor also determines a relative position between the tool-point-of-interest and the eye-tissue-of-interest.

23 Claims, 7 Drawing Sheets

(51) Int. Cl.
*A61B 34/20* (2016.01)
*A61B 90/00* (2016.01)

(52) U.S. Cl.
CPC ... *A61B 2034/102* (2016.02); *A61B 2034/105* (2016.02); *A61B 2034/2065* (2016.02); *A61B 2090/3983* (2016.02)

(56) References Cited

U.S. PATENT DOCUMENTS

| | | | |
|---|---|---|---|
| 2010/0324542 A1* | 12/2010 | Kurtz | A61F 9/008 606/6 |
| 2011/0213342 A1 | 9/2011 | Tripathi et al. | |
| 2012/0226150 A1 | 9/2012 | Balicki et al. | |
| 2012/0330129 A1 | 12/2012 | Awdeh | |
| 2014/0142591 A1 | 5/2014 | Alvarez et al. | |
| 2014/0213892 A1 | 7/2014 | Taylor et al. | |
| 2014/0221822 A1 | 8/2014 | Ehlers et al. | |
| 2014/0364870 A1 | 12/2014 | Alvarez et al. | |
| 2015/0077528 A1 | 3/2015 | Awdeh | |
| 2015/0141801 A1* | 5/2015 | Jean | A61B 5/7415 600/411 |
| 2015/0173644 A1 | 6/2015 | Ren et al. | |
| 2015/0173846 A1* | 6/2015 | Schneider | A61B 5/0066 600/424 |
| 2015/0335480 A1 | 11/2015 | Alvarez et al. | |

FOREIGN PATENT DOCUMENTS

| | | |
|---|---|---|
| CN | 103446676 A | 12/2013 |
| CN | 105828703 A | 8/2016 |

OTHER PUBLICATIONS

English Translation of Search Report (3 pages).
Japanese Office Action and English translation issued in Japanese Application No. 2018-533646, dated Aug. 10, 2021, 8 pages.
International Search Report and Written Opinion dated Apr. 2, 2017 for International Application No. PCT/IL2016/051370 (9 Pages).
An 11-page Extended European Search Report (EESR) for European patent application No. 16881397.0; the EESR was mailed from the European Patent Office (EPO) dated Jul. 12, 2019; European patent application No. 16881397.0 was filed at the EPO as a regional phase application from PCT/IL2016/051370.
Japanese Office Action issued in Japanese Application No. 2018-533646, dated Nov. 11, 2020, 7 pages.
Chinese Search Report issued in Chinese Application No. 2016800812162, dated Jul. 13, 2020, 2 pages.
English translation of the Chinese Office Action issued in Chinese Application No. 2016800812162, dated Jul. 21, 2020, 2 pages.
English translation of the Chinese Search Report issued in Chinese Application No. 2016800812162, dated Jul. 13, 2020, 2 pages.
Second Chinese Office Action issued in Chinese Application No. 2016800812162, dated Jul. 21, 2020. 3 pages.

* cited by examiner

SYSTEM AND METHOD FOR DETERMINING THE POSITION AND ORIENTATION OF A TOOL TIP RELATIVE TO EYE TISSUE OF INTEREST

CROSS-REFERENCE TO RELATED APPLICATIONS

This application is a continuation-in-part of U.S. application Ser. No. 16/066,480, filed Jun. 27, 2018 (U.S. Pat. No. 10,357,318), which is a 37 U.S.C. § 371 National Phase Application of PCT/IL2016/051370, filed Dec. 22, 2016, which claims priority to Israeli Patent Application 243384, filed Dec. 28, 2015, the contents of which are incorporated by reference herein.

FIELD OF THE DISCLOSED TECHNIQUE

The disclosed technique relates to system and method for preventing rapture of eye tissue of interest in general, and to systems and methods for determining the position and orientation of a tool tip relative to eye tissue of interest, in particular.

BACKGROUND OF THE DISCLOSED TECHNIQUE

The optical structure of the eye includes thin and fragile transparent tissues such as the cornea, the iris, the lens and the lens capsule. Common surgery procedures in ophthalmology (e.g., cataract surgery, IOL placement, cornea implantation and the like) are related to the front eye and are performed using a stereoscopic microscope. In general, the eye tissues are transparent and therefore difficult to see. These surgical procedures are complicated due to low visibility through the transparent eye tissues. During these procedures the surgeon needs to cut or avoid cutting these transparent tissues. Damage to transparent eye tissues might cause complication during the surgery, resulting long period of patient recovery, altering the outcome of the procedure and causing repeated surgeries and retirements. When a surgeon experiences difficulties in making accurate incision and procedures using the microscope, the procedure may not provide the desired results.

Prior art systems employ non-visual scanning technologies for locating the eye capsule during surgery. Reference is now made to U.S. Pat. No. 8,945,140 issued to Hubschman et al., and entitled "Surgical Procedures Using Instrument to Boundary Spacing Information Extracted from Real-Time Diagnostic Scan Data". This publication relates to a surgical method for providing a surgeon with additional guidance concerning the distance separating a working end of an instrument and the posterior capsule of the eye during a surgical procedure. The method involves acquiring non-visual three-dimensional data (i.e., diagnostic scan data), and processing the scan data for determining the distance between an instrument and the posterior boundary of the lens tissue. Visual and/or auditory conveyance of distance information is provided to the surgeon.

SUMMARY OF THE PRESENT DISCLOSED TECHNIQUE

It is an object of the disclosed technique to provide a novel method and system for determining the position and orientation of a tool tip relative to an eye tissue of interest. In accordance with one aspect of the disclosed technique, there is thus provided a system for determining a position of at least one tool point of interest of a tool, relative to an eye tissue of interest. The system includes and imager a tool tracker and a processor coupled with the imager and with the tool tracker. The imager acquires at least one image of at least one tissue reference marker. The at least one tissue reference marker is different from the eye tissue of interest. The tool tracker determines information relating to the position and orientation of the tool in a reference coordinate system. The imager and the tool tracker are in registration with the reference coordinate system. The processor determines at least one of a position and a position and orientation of the at least one tissue reference marker in the reference coordinate system, according to the acquired at least one image of the at least one tissue reference marker. The processor determines the position and orientation of the eye tissue of interest in the reference coordinate system according to the at least one of position and position and orientation of the at least one tissue reference marker and a relative position between the at least one tissue reference marker and the eye tissue of interest. The relative position is pre-determined at least from a stored 3D model. The processor further determines the position of the at least one tool point of interest in the reference coordinate system from the information relating to the position and orientation of the tool in the reference coordinate system. The processor also determines a relative position between the at least one tool point of interest and the eye tissue of interest.

In accordance with another aspect of the disclosed technique, there is thus provided a method for determining a position of at least one tool point of interest, relative to an eye tissue of interest. The method includes the procedures of acquiring at least one image of at least one tissue reference marker, determining at least one of position and position and orientation of the at least one tissue reference marker in a reference coordinate system. The at least one tissue reference marker being different from the eye tissue of interest. The method further includes the procedure of determining a position and orientation of the eye tissue of interest in the reference coordinate system according to the at least one of position and position and orientation of the at least one tissue reference marker and a relative position between the at least one tissue reference marker and the eye tissue of interest. The relative position being pre-determined at least from a stored 3D model. The method also includes the procedures of determining the position of the at least one tool point of interest in the reference coordinate system and determining a relative position between the at least one tool point of interest and the eye tissue of interest.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a system and a method for determining the position of a tool relative to eye tissue of interest. Typically, optical distortions of the cornea and the anterior chamber, inhibits determining the position thereof from acquired images. Also, specifically in the case of the posterior capsule, there is not enough information in the images (i.e., features of the tissue that are visible in both images) for determining the position of the posterior capsule, since the capsule is thin and transparent. Also, mostly the capsule center, not the capsule periphery, is directly visible to a user. According to the disclosed technique, an imager acquires at least one image of the eye and specifically of the sclera, conjunctiva, iris, cornea and the transparent tissues. The acquired image or images include a representation of a tissue reference marker or markers (e.g., the iris, a fiducial marker or markers, blood vessels) which are visible to the user and the imager. A processor determines, continuously and in real-time, at least one of the position and the position and orientation of the tissue reference marker or markers in a reference coordinate system. Also, the relative position and orientation (abbreviated herein 'P&O') between the eye tissue of interest and the tissue reference marker or markers is predetermined. The processor determines, continuously and in real-time, the P&O of the eye tissue of interest in the reference coordinate system, at least according to two factors. The first factor is the relative P&O between the eye tissue of interest and the tissue reference marker or markers and the second factor is the P&O of the tissue reference marker. The P&O of the eye tissue of interest in the reference coordinate system defines a maneuvering space in which the tool can be maneuvered without causing undesired damage to the tissue (i.e., which may or may not take into account safety distance thresholds). A tool tracker tracks (i.e., determines information relating to the P&O) of the tool in the reference coordinate system. The processor determines the distance between at least one tool point of interest (e.g., the tool tip) and eye tissue of interest and provides this determined distance to a distance indicator. The distance indicator produces an indication relating to the distance between the tool point of interest and the eye tissue of interest. The disclosure herein exemplifies a tool point of interest as the tool-tip. However, it is noted that any other point or points on the tool may be employed.

The system and method according to the disclosed technique aids surgeons or others in preventing of undesired damage to the eye tissue incision and specifically to transparent tissue. For example, during cataract surgery a lens is removed from the lens capsule, and replaced with an artificial lens. The lens is removed using a phacoemulsifciation machine which employs a phaco probe. The phaco probe includes a needle at the tip thereof which vibrates at ultrasonic frequency to sculpt and emulsify the cataract, while a pump aspirates particles through the tip. In some cases a "chopper" is employed from to aid with chopping the nucleus into smaller pieces. After removing the central lens nucleus with phacoemulsification, the softer outer lens cortex is removed with suction only. The lens tissue should be removed from the lens capsule without damaging the posterior lens capsule. However, the lens capsule is transparent and typically, surgeons have difficulty seeing it. The system and method according to the disclosed technique may be employed to track a tool such as a phaco probe to alert surgeons, for example, when the distance to the posterior eye capsule is below a predetermined threshold.

The term 'in real-time' herein above and below refers to operations (e.g., image acquisition, P&O determination) performed at a substantially high rate with regards to the system requirements (e.g., greater than 15 times per second) and at a substantially low latency relative to the system requirements (e.g., shorter than 0.1 seconds). The term 'continuously' herein above and below relates to repeatedly performing an operation (e.g., image acquisition, P&O determination) during a defined period of time.

Reference is now made to FIGS. 1A-1D, which are schematic illustrations of an exemplary system, generally referenced 100, for determining the P&O of a tool tip relative to eye tissue of interest, constructed and operative in accordance with an embodiment of the disclosed technique. Exemplary system 100 is described herein where the eye tissue of interest is the lens posterior capsule and the tissue reference marker is the iris. System 100 includes a three dimensional (3D) imager 102, a processor 104, a distance indicator 106 and a memory 108. Processor 104 is coupled with 3D imager 102, with distance indicator 106 and with memory 108.

3D imager 102 is, for example a stereoscopic imager, a structured light imager a Time-Of-Flight (TOF) imager and the like. Tool 110 includes a tool marker 112, which includes at least one marker. When tool marker 112 includes one marker, this marker should exhibit asymmetries to enable tracking in 6 Degrees Of Freedom (DOF), for example an ARUCO marker. When employing two or more markers for tracking (and imager 102 is a 3D imager), these markers may be point markers, where only the position or each marker is determined. Determining the position of two markers defines the orientation of the tool marker 112 and thus of tool 110. As such, herein above and below the term the P&O of a tool marker relates also to the position of multiple markers and the derivation of orientation therefrom. Also, the marker or markers may be active markers or passive markers. An active marker is, for example, a light emitter (e.g., Light Emitting Diode—LED) emitting light at a wavelength to which 3D imager 102 is sensitive (i.e., 3D imager 102 can acquire images of tool marker 112 and tool marker 112 is identifiable in these images). A passive marker is, for example, a reflector (i.e., a specular reflector, a retro reflector or a diffusive reflector) reflecting light impinging thereon toward 3D imager 102. The number and type of markers employed depends on factors such as the type of and the number of sensors in the imager, the shape of the tool and the required accuracy of position and orientation.

System 100 is employed for tracking (i.e., determining the P&O) of a tool 110 and specifically of the tool tip 111, relative to the anatomy of an eye 114 in general and to eye tissue of interest in particular. To that end, system 100 determines the P&O of tool marker 112 in a reference coordinate system 128 according to the images thereof acquired by 3D imager 102. Since the position of tool tip 111 relative to marker 112 is predetermined, system 100 determines the P&O of the tool tip 111.

Before describing the functionality of system 100, the following paragraph provides a brief description of eye 114. Eye 114 includes a cornea 116, an iris 118, an anterior chamber 120, a lens capsule 122, a lens 124, and a retina 126. Cornea 116 is a transparent front part of eye 114 that covers iris 118 and anterior chamber 120. Cornea 116 with anterior chamber 120, lens 124, refract light onto retina 126. Iris 118 is a thin circular structure responsible for controlling the diameter and size of a pupil (not shown) and thus the amount of light reaching retina 126. That is, iris 118 is the aperture stop and the pupil is the aperture. Anterior chamber 120 is a space between iris 118 and the inner surface of cornea 116, filled with aqueous humor. Lens capsule 122 completely surrounds lens 124. Also, lens capsule 122 in general, and the posterior capsule in particular is a clear (i.e., transparent), membrane structure. Lens capsule 122 assists in shaping lens 124 and the surface curvature thereof. Lens 124 is a transparent, biconvex structure that helps (along with cornea 116) to focus light passing there through on retina 126. Retina 126 is the inner coat of the globe of eye 114, and is a light-sensitive layer of tissue.

Memory 108 stores information relating to the relative P&O between an iris and a lens capsule. This relative P&O is substantially constant. Memory 108 may further store information relating to the shape and size of a lens capsule. This stored information is employed to define a 3D model of a lens capsule. This stored 3D model is, for example, a generic model of the eye, a pre-operative Optical Coherence Tomography (OCT) image, a 3D ultrasonic image. From this stored 3D model, information relating to the geometrical structure and the eye tissue of interest (e.g., the posterior lens capsule, the retina) may be derived. Also, the 3D model includes representation of the tissue reference marker. As such, information relating to the relative position and orientation between the eye tissue of interest and the tissue reference marker may be determined. During a procedure, 3D imager 102 continuously acquires 3D images of iris 118. 3D imager 102 provides the acquired 3D images to processor 104. Processor 104 determines, continuously and in real-time, the P&O of iris 118 in reference coordinate system 128 according to the acquired images. Processor 104 then determines, continuously, in real-time, the P&O of lens capsule 122 in reference coordinate system 128, according to determined P&O of iris 118, and according to the relative P&O between an iris and the lens capsule, and specifically the posterior capsule. The relative P&O between the iris and the posterior lens capsule is determined from the stored 3D model in memory 108. Thus, processor 104 determines an allowed maneuvering space in which the tool 110 can be maneuvered 110 without causing undesired damage to the tissue.

When either tool 110 or another tool (i.e., which is also fitted with a marker similar to tool marker 112) is inserted into lens 124 (i.e., either manually or automatically), 3D imager 102 acquires real-time images of tool marker 112 and provides the acquired real-time images to processor 104. Processor 104 determines the position of the tool tip 111 in reference coordinate system 128 in real-time. Then, processor 104 determine the distance between the tool tip 111 and lens capsule 122 and provides this determined distance to distance indicator 106. This distance is, for example, the smallest distance to lens capsule 122 or the distance between tool tip 111 and lens capsule 122 in the direction in which tool tip 111 is oriented. Distance indicator 106 produces an indication relating to the distance between the tool tip 111 and the boundaries of lens capsule 122. As mentioned above, the tool tip is brought above and below as an example for a tool point of interest. According to another example a plurality of tool points of interest may be selected and the distance between these points to the closest eye tissue is determined and an indication relating thereto produced.

The indication produced by distance indicator 106 may be a visual indication such as a numerical representation of the distance, distance bars and the like. As a further example, the visual indication may be presented on a display (e.g., a LCD screen, Heads-Up-Display, Near-To-Eye display and the like). The visual indication may also be a 3D model (i.e., either the above mentioned stored model or a different model) of the eye along with a symbol of tool 110. The P&O of the symbol of tool 110 on the display, relative to the position of the 3D model of the eye corresponds to the relative P&O between tool 110 and lens capsule 122. The visual indication may further include a flashing symbol, where the flashing frequency is inversely proportional to the distance between tool tip 111 and the lens capsule 122. The indication may be alternatively or additionally be an audio indication such as a sound with a pitch or volume or both, which varies according to the distance. The sound can be also of voice indicating the distance or warning following the distance to the capsule. As a further alternative or in addition, distance indicator 106 may indicate that the distance between the tool tip 111 and lens capsule 122 is below a threshold. In the example brought forth hereinabove, the processor determines the entire lens 124 as the maneuvering space in which the tool 110 can be maneuvered 110 without causing undesired damage to the tissue (i.e., without taking into account safety thresholds). However, this maneuvering space may be further limited (i.e., taking into account safety thresholds). For example, with reference to FIG. 1D, processor 104 may define a virtual boundary 130 relating to lens capsule 122 or a portion thereof. This virtual boundary further limits the maneuvering space in which the user may maneuver tool 110 without causing undesired damage to the tissue. When tool 110 crosses that virtual boundary, an indication is produced as described above. This virtual boundary may also be displayed to the user as part of the above mentioned 3D model.

As mentioned above, tool 110 may move automatically. For example, tool 110 is attached to a robot (not shown), such a robotic arm, which is coupled with processor 104. Typically, the robotic arm includes a dedicated control system which is coupled with processor 104. Processor 104 instructs the robot control system to move the robot arm and thus tool 110 toward lens capsule 122 according to the P&O of tool 110 and of lens capsule 122. Processor 104 may further instruct the robot control system to stop the robot arm, for example, when the distance between the tool tip 111 and lens capsule 122 is below a threshold. Alternatively the motion of the robotic arm may be controlled by the user.

To track the P&O of the anatomical reference markers, 3D imager 102 periodically acquires information relating to P&O of these anatomical reference markers. It is noted that the reference markers in general and the anatomical reference markers in particular may be point markers. As, such only the position thereof can be determined. However, the orientation of the eye can be determined by employing three or more such point reference markers. Therefore, herein above when a plurality of such anatomical reference markers are employed, the orientation of the eye may be determined from these positions. As such, herein above and below the term the P&O of a reference marker relates also to the position of multiple markers and the derivation of orientation therefrom. Processor 104 determines the P&O of the anatomical reference markers in reference coordinate system 128. Processor 128 updates the P&O of the stored model according to the P&O of the anatomical reference markers.

When determining the P&O of lens capsule 122 in real-time, processor 104 may further employ the above mentioned positions of tool tip 111, when tool tip 111 is in contact or in close contact with outer and inner boundaries of lens capsule 122, to improve the accuracy of the determined P&O of lens capsule 122 (e.g., by employing the locations of these boundary points as constraints).

Modeling lens capsule 122 prior to the procedure may also be achieved by employing imaging techniques. For example, prior to the procedure an Optical Coherence Tomography (OCT) image or an ultrasound image of the eye is acquired (i.e., a model image). This image includes a representation of lens capsule 122. The geometrical structure and the size of lens capsule 122 may be derived from such images by employing image processing techniques. Also the relative P&O between the iris 118 and lens capsule 122 may be determined from the acquired images when both lens capsule 122 and the iris 118 are visible in the model image. It is noted that in general, modeling lens capsule 122 and determining the P&O of iris 118 may be done sequentially or concurrently.

As described above, processor 104 employs iris 118 as tissue reference marker and determines the P&O of the iris 118 in reference coordinate system 128. However, the tissue reference marker may be any marker detectable by 3D imager 102, where the relative P&O between the lens capsule 122 and the marker or anatomical reference markers is predetermined. For example, the tissue reference marker may be conjunctiva, blood vessels within the conjunctiva or within other organs of the eye. Alternatively, the tissue reference marker can be an artificial marker (e.g., fiducial marker) placed on the eye. For example, the tissue reference marker is patch attached to lens capsule 122 when the boundaries of lens capsule 122 are determined. As a further example, the tissue reference marker is drawn on the eye by a dedicated marker pen. To determine the P&O of the tissue reference marker in the acquired 3D image, processor 104 employs image processing techniques. For example, when the tissue reference marker is iris 118, processor 104 identifies the iris in the acquired 3D image by identifying a black circle which relates to the pupil encircled by a first ring, which relates to the iris, encircled by a second ring which relates to the limbus. Thus, the iris pattern and shape provide a discernible tissue reference marker for the system. The P&O of the first ring relates to the position of iris 118.

Figure 1A:
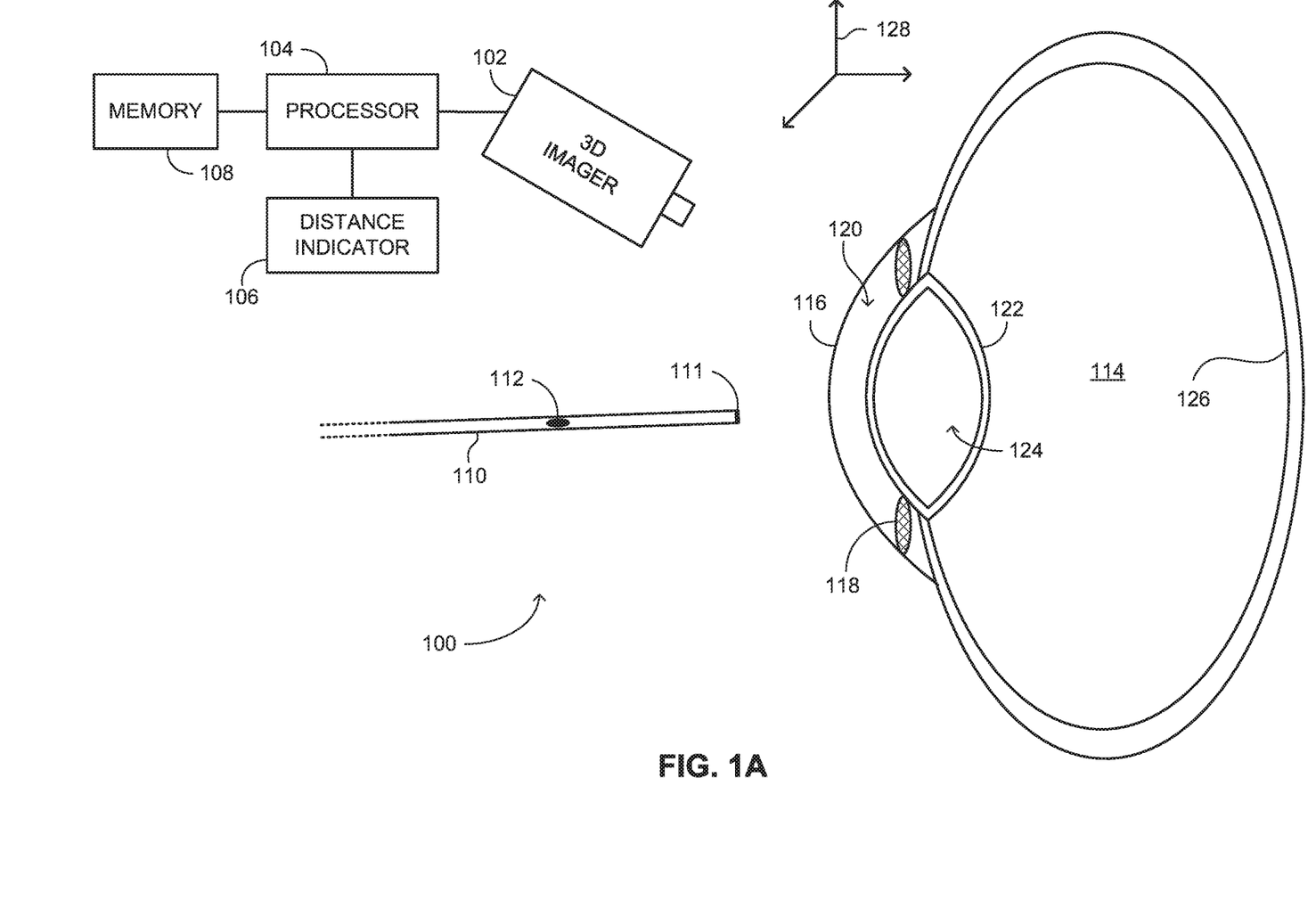
FIGS. 1A-1D are schematic illustrations of an exemplary system for determining the position and orientation of a tool tip relative to eye tissue of interest, constructed and operative in accordance with an embodiment of the disclosed technique.
Figure 1B:
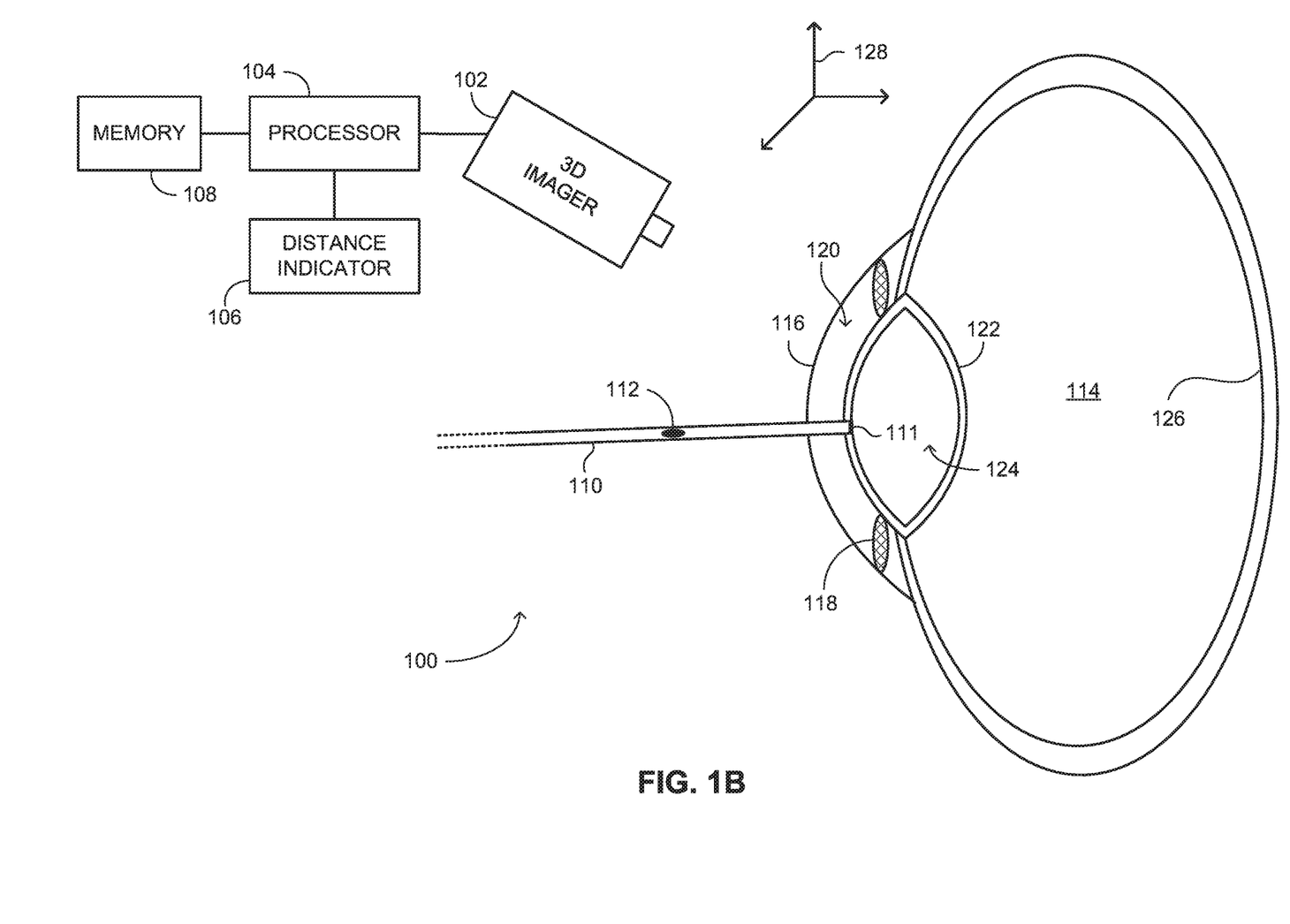
Figure 1C:
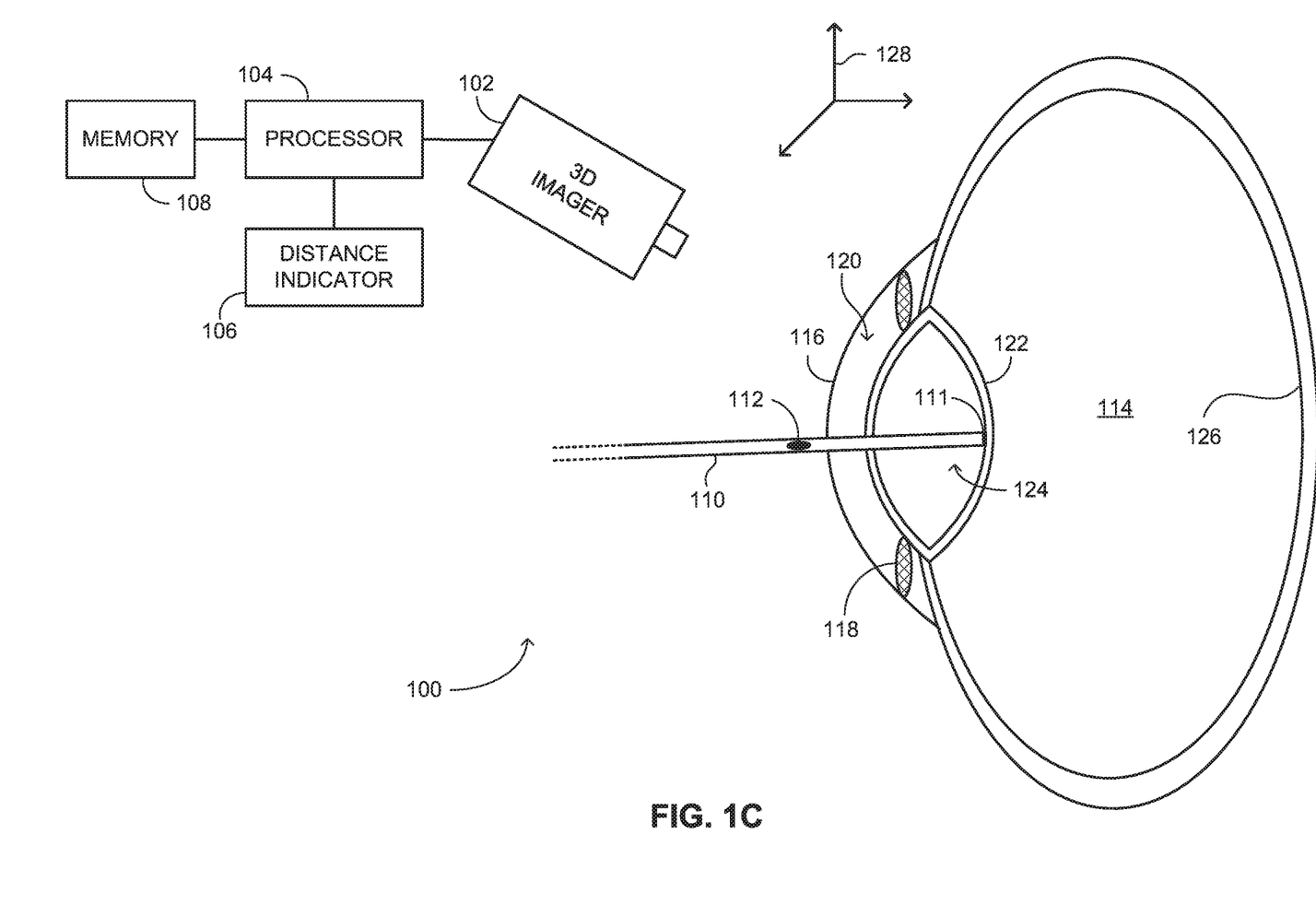
Figure 1D:
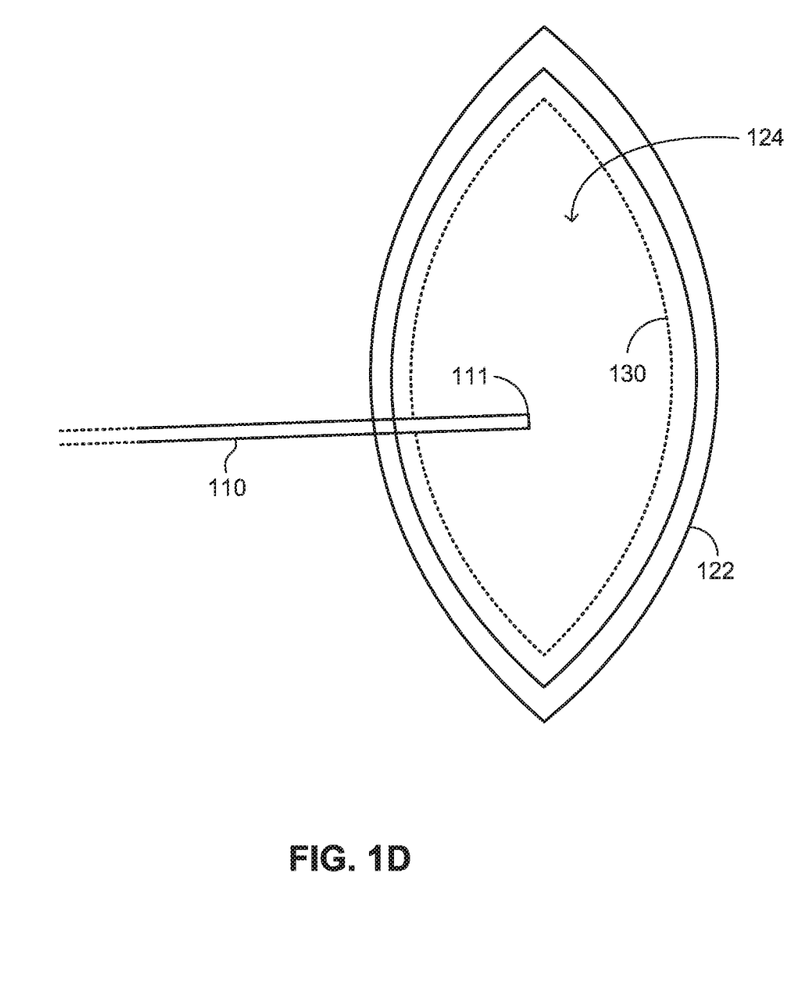

The system described herein above in conjunction with FIGS. 1A-1C relates to an exemplary system in which a 3D imager is employed for imaging as well as for tracking and where the eye tissue of interest is the lens capsule and the tissue reference marker is the iris. In general, a system according to the disclosed technique may employ various techniques for tracking a medical tool such as optical tracking, electromagnetic tracking, ultrasound tracking and inertial tracking. Furthermore, as mentioned above, the 3D imager may be any one of various 3D imagers such as stereoscopic camera, structured light imager or a TOF camera. Alternatively, the imager may be a two dimensional (2D) imager. When the imager is a 2D imager at least three artificial markers are placed on the eye.

Figure 2:
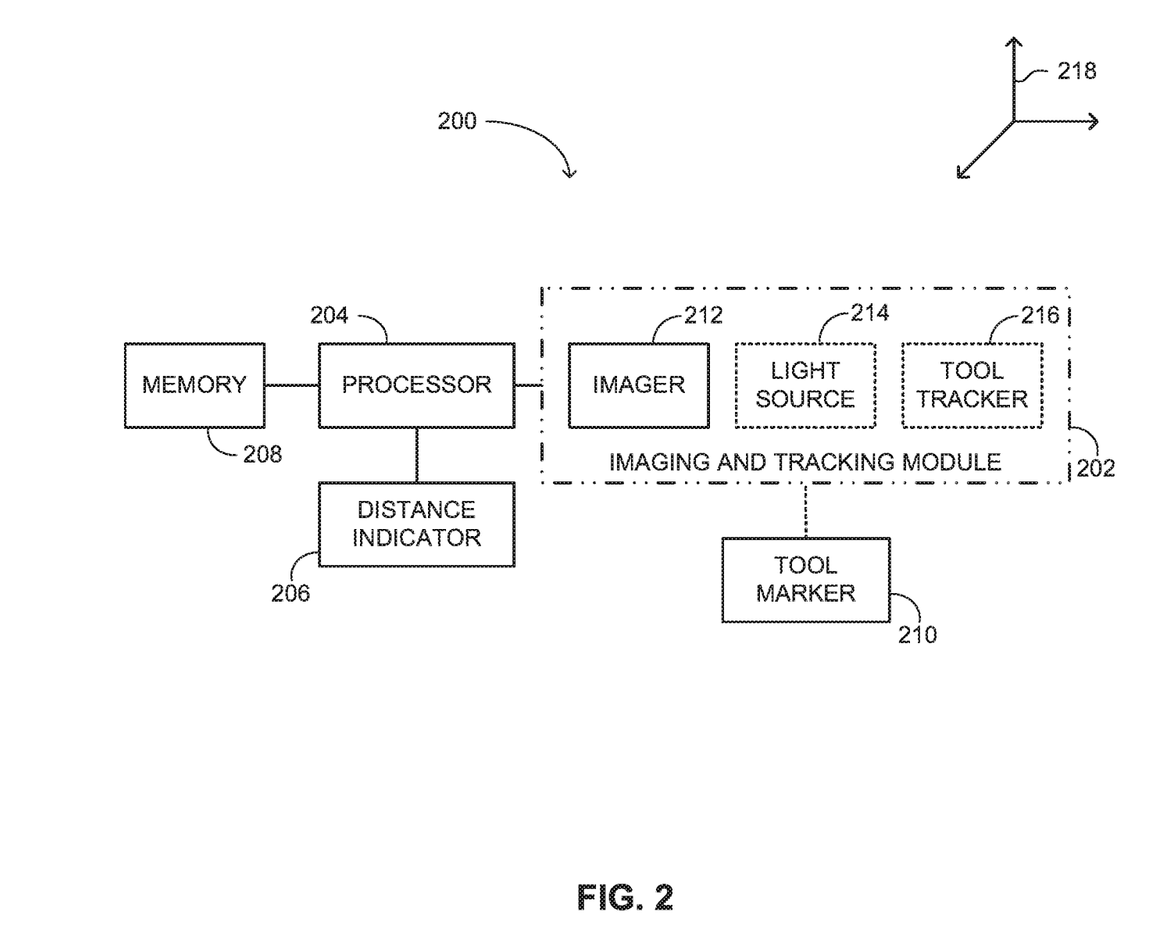
FIG. 2 is a schematic illustration of system for determining the position and orientation of a tool tip relative to eye tissue of interest, constructed and operative in accordance with another embodiment of the disclosed technique.

Reference is now made to FIG. 2, which is a schematic illustration of a system, generally referenced 200, for determining the P&O of a tool tip relative to the eye tissue of interest, constructed and operative in accordance with another embodiment of the disclosed technique. The operation of system 200 is similar to the operation of system 100 described above in conjunction with FIGS. 1A-1C. System 200 includes an imaging and tracking module 202, a processor 204, a distance indicator 206, and memory 208 and a tool marker 210. Imaging and tracking module 202 at least includes an imager 212. Imager 212 may be a 3D imager or a 2D imager. Imaging and tracking module 202 optionally includes a light source 214 and a tool tracker 216 (i.e., as indicated by the hatched lines). Processor 204 is coupled with imaging and tracking module 202, with distance indicator 206 and with memory 208. Tool marker 210 is similar to tool marker 112 (FIGS. 1A-1C) discussed above and is optically detected by imaging and tracking module 202.

When imager 212 is a 3D imager, imager 212 acquires a 3D image or images of the eye. The term '3D image' relates herein above and below relates to image data which includes information relating to the P&O (i.e., in a reference coordinate system) of the various features in the scene. When imager 212 is a 3D imager, imager 212 may be embodied as a stereoscopic camera, which acquires two images of the eye from two different perspectives. When imager 212 is a stereoscopic camera, light source 214 is optional. Imager 212 may alternatively be embodied as a structured light imager. In such a case, light source 214 illuminates the eye with structured light and imager 212 acquires an image (i.e., may be a two-dimensional image) of the illuminated eye (i.e., with the structured light). According to another alternative, imager 212 may be a TOF camera. Accordingly, light source 214 emits temporal pulse of light toward the eye. Imager 212 is time synchronized with light source 214 and acquires an image or images of the eye. Imager 12 integrates light only when the light pulse is expected to reflect back to the imager. The difference between the time light source 214 emits a pulse and the time imager 212 acquires an image of the reflected light pulse is related to the distance between imager and tracking module 202 and the object being tracked. When imager 212 is a 2D imager, imager 212 acquires a 2D image or images of at least three artificial tissue reference markers placed on the eye. The relative positions between the artificial markers are known (e.g., stored in memory 208 when a relatively high degree of accuracy is require). Alternatively, the relative positions between the markers are determined, for example, by placing the tool tip on each marker, determining the position of each marker in reference coordinate system 218 and determining the relative positions between the markers accordingly.

In general, tool tracker 216 at least acquires information relating to the P&O of tool marker 210 in reference coordinate system 218. According to one alternative, similar to as described above in conjunction with FIG. 1A-1C, tool tracker 216 and imager 212 are one and the same. Accordingly, similar to as described above, tool marker 210 is an active or a passive marker. For example, tool marker 210 is an array of LEDs or fiducial markers located on the tool and identifiable in an image acquired by imager 212. Tool marker 210 is thus optically detected by imaging and tracking module 202 and the P&O tool marker 210 is determined according to the images acquired by imager 212. According to another alternative, tool tracker 216 is an optical tracker different from imager 212. In both cases the information relating to the P&O of tool marker 210 are images of tool marker 210. Tool tracker 216 may also track the tool according to the shape thereof. The shape of the tool maybe stored in memory 208 based on a tool model acquired during a preliminary learning stage of system 200. Accordingly, imager 212 acquires 3D image of the tool.

According to a further alternative, tool tracker 216 is an electromagnetic tracker and tool marker 210 is at least one electromagnetic sensor (e.g., coils, Hall Effect sensors). Tool marker 210 is electromagnetically detected by imaging and tracking module 202 and the P&O of tool marker 210 is determined according to the measurements of a magnetic field by the electromagnetic sensors. The electromagnetic field is generated by tool tracker 216.

According to yet another alternative, tool tracker 216 is an ultrasonic tracker and tool marker 210 includes at least one ultrasonic transducer and tool tracker 216 includes at least three ultrasonic receivers. Tool marker 210 is thus c ultrasonically detected by imaging and tracking module 202 and the P&O of tool marker 210 is determined according to the measurements of a the time elapsed between the transmission and reception of the sound and the velocity of sound in the medium.

According to yet another alternative, tool tracker 216 is an inertial navigation system and tool marker 210 is an Inertial Measurement Unit (IMU). Tool marker 210 provides information regarding the linear acceleration and rotational velocity of the tool and tool tracker 216 determines the P&O of tool marker 210 accordingly relative to an initial known reference. Such an IMU may be implemented as Microelectromechanical Systems (M EMS) sensors (e.g., gyroscopes and accelerometers) along with a corresponding integrated circuit. It is, however, noted that, typically, inertial navigation systems are employed in hybrid configurations in conjunction with at least another tracking system.

It is also noted that the coordinate system associated with imager 212 and the coordinate system associated with tool tracker 216 are registered with each other to define reference coordinate system 218 (e.g., during the manufacturing process or by calibration process). In other words, imager 212 and tool tracker 216 are in registration with reference coordinate system 218. Thus, an image acquired by imager 212 is also registered in reference coordinate system 218 and the information relating to the P&Os of tool marker 212, and consequently of other related positions (e.g., the tool tip), is also acquired in reference coordinate system 218. Specifically, when imager 212 is a 3D imager, any feature directly visible by imager 212 may be identified and the position thereof related to a position in the tracker coordinate system. Such a feature may be used as an anatomical reference marker.

According to one embodiment, processor 204 determines the P&O of tool marker 210 according to information relating to the P&O of tool marker 210 provided by tool tracker 216. Alternatively, tool tracker 216 determines the P&O of tool marker 210 and provides the determined P&O to processor 204. In both cases, processor 204 determines the position of the tool tip and the distance between the tool tip and the eye tissue of interest.

Processor 204 includes components required for performing computing operations, such as a central processing unit that may be implemented with a conventional microprocessor, a random access memory (RAM) for temporary storage of information, and a read only memory (ROM) for permanent storage of information. A memory controller is provided for controlling RAM. A bus interconnects the components of the processor system. A bus controller is provided for controlling the bus. An interrupt controller is used for receiving and processing various interrupt signals from the system components. Mass storage may be provided by a Hard Disc Drive (HDD) or by a flash drive. The processor system further includes a network interface that allows the system to be interconnected to a local area network (LAN) or a wide area network (WAN). Operation of the processor is generally controlled and coordinated by operating system software that can be stored on the memory. Processor 204 provides this determined to distance indicator 206. Distance indicator 206 provides an indication of the distance between the tool tip and the eye tissue of interest similar to as described above.

During a procedure, imager 212 continuously acquires images of the tissue reference marker or markers. Imager 212 provides the acquired images to processor 204. The acquired images include information relating the position and orientation of the tissue reference marker or markers. For example, when imager 212 is a stereoscopic camera, the relation between the position of an image-feature in an image acquired by one camera, and the position of the same image-feature in an image acquired by the second cameral, is associated with the position of the actual feature in reference coordinate system 218. By identifying the image-features associated with the tissue reference marker or markers, the position and orientation thereof, in reference coordinate system 218 may be determined. When imager 212 is a 2D imager, imager 212 acquires an image of at least three artificial markers. The image pixel location of each marker is associated with two angles (i.e., a horizontal angle and a vertical angle measured from the center of the imaging sensor). In essence, these angles, along with the known, relative position between the tissue reference markers, define six equations with six unknowns (i.e., three for position and three for orientation). Thus, processor 204, continuously and in real-time, determines the P&O of the tissue reference marker in a reference coordinate system 218 according to the acquired images. Processor 204 then determines, continuously and in real-time, the P&O of the eye tissue of interest in reference coordinate system 218, according to determined P&O of the tissue reference marker and according to the stored relative P&O between tissue reference marker or markers and the eye tissue. Thus, processor 204 determines a maneuvering space in which the user may maneuver tool 110 in which the tool can be maneuvered without causing undesired damage to the tissue (i.e., which may or may not take into account safety distance thresholds).

Processor 204 determines the position of the tool tip in real-time and determines the distance between the tool tip and the eye tissue of interest. Processor 204 provides this determined distance to distance indicator 206. Distance indicator 206 provides an indication of the distance between the tool tip and the eye tissue of interest similar to as described above. Similar to system 100, a maneuvering space in which the user may maneuver the tool in, which the tool can be maneuvered without causing undesired damage to the tissue take into account safety distance thresholds, for example, by defining a virtual boundary relating to the eye tissue of interest. When the tool crosses that virtual boundary, an indication is produced a described above.

When the stored 3D model is a generic model, the accuracy of the estimation of the geometrical structure, the size, the position and the orientation of eye tissue of interest in reference coordinate system 218, may be improved by modeling the eye tissue prior to the procedure. To that end, modeling the eye and the eye tissue of interest prior to the procedure may be achieved by employing imaging techniques. For example, prior to the procedure an Optical Coherence Tomography (OCT) image or an ultrasound image of the eye is acquired (i.e., a model image). This model image includes a representation of the eye tissue of interest. The geometrical structure and the size of the eye tissue of interest may be derived from such images by employing image processing techniques. When both the eye tissue of interest and the tissue reference marker are visible in the model image, the relative P&O between the tissue reference marker (i.e., either anatomical or biological) and the eye tissue of interest may be determined from the acquired images employing image processing techniques.

In some cases, anatomical reference markers other than the iris (e.g., blood vessels on the sclera) can be employed as reference markers. Such anatomical reference markers are, for example, blood vessels or apparent intersections between blood vessels visible on the sclera. In general, these reference markers may be a visible point. However, the stored 3D model may not include a representation of these anatomical reference markers, which typically do not exist in such models. To employ such reference markers that are not visible in the stored 3D model, the 3D model is initially registered in reference coordinate system 218 (i.e., every point in the model of the eye should be associated with corresponding coordinates in reference coordinate system 218) by fitting the stored 3D model with a measured intra-operative model of the eye. Thus, the 3D model is in registration with reference coordinate system 218. Concurrently with the registration process, the position of the selected anatomical reference markers, in reference coordinate system 218, is determined from an image or images acquired by imager 212. Consequently, the position of the stored 3D model relative to these reference markers is also determined. Thereafter, the selected anatomical reference markers are tracked in reference coordinate system 218 and the P&O of the stored 3D model may be updated according to the changes in the P&O of the selected anatomical reference markers. When the anatomical reference markers are points, only the position thereof can be determined. However, when a plurality of such anatomical reference markers are employed, the P&O of the stored 3D model may be determined based on the positions respective of the plurality of anatomical reference markers. Specifically, if the position of any point in the 3D model is known relative to at least three point reference markers at the moment of registration, an updated position of the 3D model may be determined at any time based on the updated positions of the three point reference markers The 3D model is initially and momentarily registered in reference coordinate system 218, by fitting the stored 3D model with a measured intra-operative model of the eye, where the intra-operative model and the stored 3D model include representation of common portions of the eye. According to the disclosed technique for determining the measured intra-operative model, the user positions a tool tip of a modeling tool at a plurality of points on the eye tissue (e.g. the anterior capsule, the anterior cornea), the stored 3D model include representation of these plurality of points. For example, the user slides the modeling tool tip on the tissue. Tool tracker 216 acquires information relating to the P&O of tool marker 210 and thus of the position of the modeling tool tip at each of these plurality of points. Processor 204 determines the position of the tool tip in reference coordinate system 218. Processor estimates a measured intra-operative model of the eye tissue from the positions of the tool tip at each of these plurality of points (i.e., also in reference coordinate system 218), for example, by employing polygonal modeling. It is noted that the measured intra-operative model may be a model of only a portion of the eye. Processor 204 registers momentarily the stored model of the eye (i.e., when the eye does not move) with the measured intra-operative model, for example, by fitting the measured intra-operative model to the stored model. Since the measured intra-operative model is determined in reference coordinate system 218 the stored model is also registered in reference coordinate system 218, once registered with the measured model. Furthermore, concurrently with the process of positioning the tool tip at a plurality of points on the eye tissue when measuring the (measured) intra-operative model, processor 204 determines the P&O of the selected anatomical reference markers in reference coordinate system 218. When imager 212 is a 3D imager, processor 204 determines the P&O of the anatomical reference markers in reference coordinate system 218 from a 3D image or images thereof. Once the position of the selected anatomical reference markers in reference coordinate system 218 is known and the stored 3D model is registered in reference coordinate system 218, processor 204 determines the position of the stored 3D model relative to the reference markers and the relative position between the eye tissue of interest and the anatomical reference markers. Thereafter, as described above, the selected anatomical reference markers are tracked (i.e., since the eye may move) in reference coordinate system 218 (e.g., from images acquired by imager 212) and the P&O of the stored 3D model is updated according to the changes in the P&O of the selected anatomical reference markers. In other words, the registration of the stored 3D model in reference coordinate system 218 is updated according to changes in the P&O of the selected anatomical reference markers. It is noted that in order to register the stored model in reference coordinate system 218, the measured model should exhibit asymmetry. However, even if the measured model exhibits symmetry, as might be the case when the anterior cornea or the anterior capsule are used, registration in 5 DOF could still be achieved and employed. For example, for registering 3 position coordinates as well as pitch and yaw (i.e., two orientation coordinates) since the lens capsule may also be symmetric in the roll angle.

As mentioned above, the eye tissue of interest is, for example the retina. In such a case, the reference marker or markers are preferably located on the sclera (e.g., a fiducial marker or blood vessels) and the P&O of the retina is calculated relative thereto. Processor 204 determines the P&O of the tool in real-time and determines the distance between the tool tip and the retina. Processor 204 provides this determined distance to distance indicator 206. Distance indicator 206 provides an indication of the distance between the tool tip and the eye tissue of interest similar to as described above.

Figure 3:
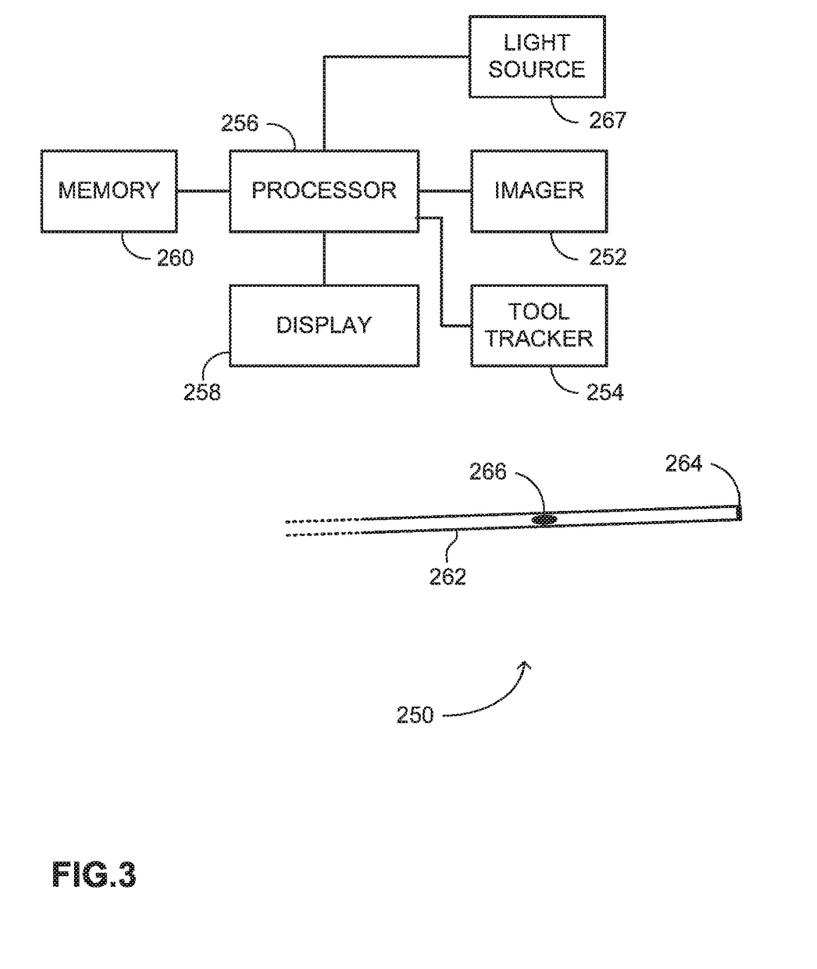
FIG. 3 is a schematic illustration of system for determining the position and orientation of a tool tip relative to eye tissue of interest, constructed and operative in accordance with a further embodiment of the disclosed technique.

Reference is now made to FIG. 3, which is a schematic illustration of an imaging and tracking system, generally referenced 250, for imaging the eye during a surgical procedure and determining the P&O of a tool relative to the eye tissue of interest, constructed and operative in accordance with a further embodiment of the disclosed technique. Specifically and as further elaborated below, system 250 may be employed as a surgical microscope, while tracking the tool or tools employed during the surgical procedure. As further elaborated below, system 250 may augment navigational information relating to the tool (e.g., P&O of tool, trajectory of tool, target location) on the image or images displayed to the user. System 250 includes an imager 252, a tool tracker 254, a processor 256, a display 258 and a memory 260. Optionally, system 250 includes a tool marker 266 and a light source 267. Similar to as described above in conjunction with imager 212 (FIG. 2), imager 252 may be a 3D imager or a 2D imager. Tool tracker 254 is, for example, an optical tracker, an electromagnetic tracker, an ultrasonic tracker, an inertial tracker or a hybrid tracker which includes any combination of the above mentioned trackers. Processor 256 is coupled with imager 252, with tool tracker 254 with display 258 and with memory 260. Tool tracker 254 acquires information relating to the P&O of tool marker 266, and thus of tool 262 in reference coordinate system 268. Either tool tracker 254 or processor 256 (i.e., depending on implementation details) determines the P&O of tool 262 in reference coordinate system 268.

When the P&O of imager 252 in reference coordinate system 268 is known, then the position (i.e., in reference coordinate system 268) of each directly visible point in the Field Of View (FOV) of imager 252, and thus of a visible 3D model, can also be determined. In other words, the coordinate system of the image or images acquired by imager 252 and referenced coordinate system 268 are registered with each other. Preferably, the P&O of imager 252 in reference coordinate system is pre-determined in the manufacturing or installment stage of the system. Alternatively, or when the pre-determined registration is rendered unreliable (e.g., when one of the modules was replaced) then, reference markers, identifiable in the acquired 3D image and directly seen by the user may be employed to register the 3D image with reference coordinate system 268. To that end, the position of these reference markers in the image coordinate system is determined, for example, by employing image processing techniques (e.g., segmentation, correlation and the like). Also, the position of these markers in the reference coordinate system is also determined, for example, by placing the tip of tool 262 on each of the reference markers and determining the position of the tip of tool 262. Since each marker has a corresponding position in the image coordinate system and in the reference coordinate system, these two coordinate systems can be registered such that each point in the 3D image has a corresponding point in reference coordinate system 268. These reference markers may be artificial markers such as explained above or naturally occurring reference markers (e.g., blood vessels visible on the sclera).

When imager 252 is a stereoscopic camera, imager 252 includes two camera's, a right camera and a left camera, each acquiring a respective image from a respective perspective, forming a stereoscopic image pair, where one image is intended to be displayed to the left eye and the other image is intended to be displayed to the right eye. In such a case, display 258 is, for example, a stereoscopic display which includes two eyepieces, a left eyepiece and a right eyepiece. Each eyepiece receives a respective image. Typically, the image acquired by the left camera is provided to the left eyepiece and the image acquired by the right camera is provided to the right eyepiece. In some cases (e.g., in procedures which include a wide lens viewing system) the image acquired by the left camera is provided to the right eyepiece and the image acquired by the right camera is provided to the left eyepiece. In both cases, the brain of the user combines these two images to form a 3D image of the scene. According to other examples, display 258 is a monitor displaying an anaglyph of the two images or polarized images and the user employs 3D glasses to present the respective image to the respective eye. Thus, when a procedure is performed on the eye, imager 252 and display 258 can operate as an operating microscope enabling the user to view the pertinent eye parts and tissue (e.g., the retina, cornea and the like).

Tool tracker 254 at least acquires information relating to the P&O of tool marker 266 in reference coordinate system 268. Therefrom, the position of the tool tip, or other portions of the tool, can also be determined (i.e., either directly by tool tracker 254 or by processor 256). To determine the P&O of tool 262, either tool tracker 254 or processor 256 (i.e., depending on the implementation), solves at least six equations with six unknowns (e.g., three unknowns for position, the x, y and z coordinates and three unknowns for orientation, the azimuth elevation and roll angles). Following is an example where tool tracker 254 is an optical tool tracker employing an out-in configuration with a 2D imager, where tool marker 266 includes three light emitters and where the relative position between these three light emitters is known. The light emitters may be active marker or a passive marker. Also the 2D imager employed for tracking may be sensitive in to one band (e.g., IR), while and imager 252 is sensitive in another band (e.g., visible). Thus, the light employed for tracking (i.e., either actively or passively) does not interfere with the images acquired by imager 252. When tracking tool 262, the 2D imager of tool tracker 254 acquires an image of the light emitters of tool marker 266. Each representation of a light emitter in the acquired image is associated with two angles. For example, when the optical imager is a Charge Coupled Device (CCD) sensor, that CCD sensor is associated with a physical center. An imaginary line passing through this physical center, perpendicular to the sensor plane, defines the optical axis of the CCD sensor. Each pixel in CCD sensor is associated with a respective location on the CCD sensor, defined by a sensor 2D coordinates system in pixel units (e.g., a pixel located at coordinates [2;3] in the sensor 2D coordinates system is the pixel at the intersection of the second colon of pixels with the third row of pixels). Accordingly, each pixel is associated with a horizontal angle and a vertical angle from the optical axis of the sensor, related to the location of the pixel in the sensor 2D coordinate system. Consequently, each representation of a light emitter determined from an image acquired by the CCD sensor is also associated with a respective horizontal angle and a vertical angle from the center of the optical axis of the CCD sensor. Since tool marker 266 includes three light emitters, each associated with two angels, a total of six measurements of angles are acquired. Since the relative position between the light emitters is also known, these measurements define the above mentioned six equations with six unknowns. Solving these equations determines the position and orientation of tool marker 266 in reference coordinate system 268 and thus of tool 262. In general, tool tracker 254 can track the P&O of multiple different tools, which could be employed during a procedure.

An alternative optical tracking system may track the tool 262 according to the shape of tool 262. To that end, a 3D tool model of tool 262 is stored in memory 260. The 3D tool model is acquired during a preliminary learning or calibration stage, or may be a predetermined model provide by the manufacturer of tool 262. Every P&O of tool 262 in reference coordinate system 268 exhibits a unique projection of tool 262 on the imager of tool tracker 254. To determine the P&O of tool 262, the imager of tool tracker 254 acquires an imager of tool 262. Then, employing the stored 3D tool model, processor 256 or tool tracker 254 (i.e., depending on the implementation), searches for a P&O of the of the stored 3D tool model, which results in a projection which best correlates with the acquired image of tool 262. The P&O which best correlates with the acquired image of tool 262 is determined as the P&O of tool 262. It is noted that to track tool 262 in 6 Degrees Of Freedom (DOF), tool 262 should be asymmetrical about all three axis. However, even when tool 262 exhibits symmetry about one axis, tracking tool 262 in 5 DOFs is still possible and in many cases sufficient, for example, when information relating to the rotation of tool 262 is not required.

Both of the above examples for tracking tool 262 (i.e., either by employing tool markers or by employing a tool model) were described with the use of a single imager. However, to increase the accuracy of the tracking information, two or more imagers may be used. In other words, tool tracker 254 includes two or more imagers.

Similar to system 100 (FIGS. 1A-1D) and system 200 (FIG. 2) described above, system 250 tracks the P&O of tool 262 in reference coordinate system 268. Also, since a 3D model of the eye (i.e., either the stored 3D model or the measured intra-operative model) is registered in reference coordinate system 268, information relating to the medical procedure may be presented to the user via display 258. For example, an image including a graphical representation of tool 262 overlaid on an image of the 3D model of the eye, at the corresponding apparent position and orientation of tool 262 may be displayed to the user on display 258. Such an overlaid image presents the user with information relating to the position and orientation of tool 262 relative to various locations of the eye (i.e., which are included in the 3D model). Furthermore, navigational information relating the tool 262 may be presented to the user. This navigational information includes, for example, a line representing the trajectory of the tool or a target location (i.e., the point to which the tool is intended to reach) and the like. Similar to as described above, processor 256 can also determine the distance between tool tip 264 and an eye tissue of interest and provide an indication (e.g., on display 258) when the tool tip 264 is close to a target position or to an undesired position.

Figure 4:
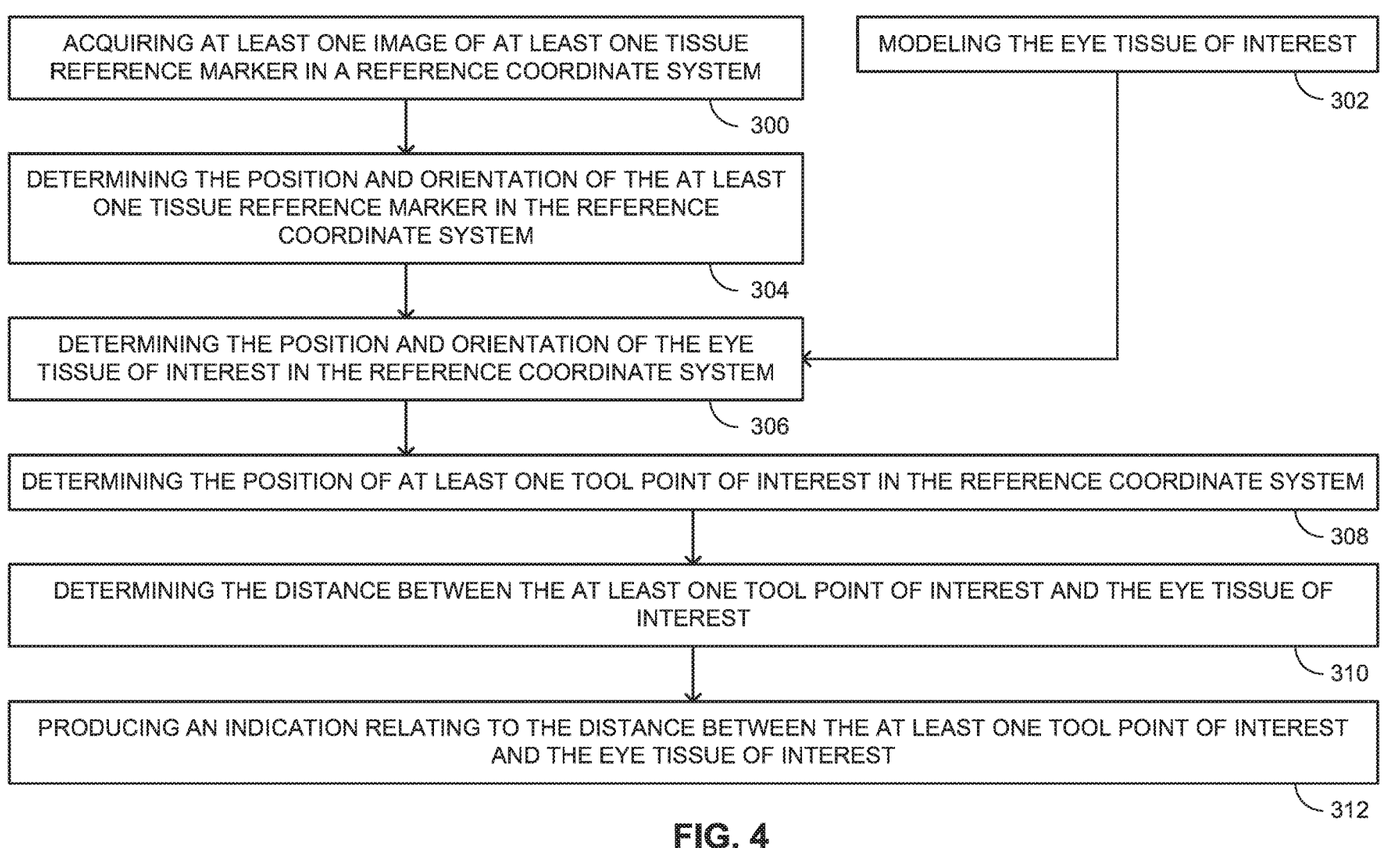
FIG. 4 is a schematic illustration of method for determining the position and orientation of a tool tip relative to eye tissue of interest, operative in accordance with another embodiment of the disclosed technique.

Reference is now made to FIG. 4, which is a schematic illustration of a method for determining the position and orientation of a tool tip relative to the an eye tissue of interest, operative in accordance with another embodiment of the disclosed technique. In procedure 300, at least one image of at least one tissue reference marker is acquired in a reference coordinate system. The image or images may be 2D images or 3D images. The 3D images may be a stereoscopic image, a structured light image or a TOF image. When the image or images are 2D images, at least three tissue reference markers are employed. With reference to FIG. 2, imager 212 acquires an image of at least one tissue reference marker. After procedure 300, the method proceeds to procedure 304.

In procedure 302, the eye tissue of interest is modeled. The eye tissue of interest is modeled, for example, improving the accuracy of a priori information relating to estimations of the P&O, the geometrical structure and the size of the eye tissue of interest, by determining position, and optionally the orientation of the tool tip when the tool tip is in contact or in close contact with points on the tissue. Alternatively, the eye tissue of interest is modeled by employing imaging such as OCT or ultrasound imaging. For example, With reference to FIGS. 1A-1C and 2, processor 204 determines a model of the eye tissue of interest. To that end, tool 110 moves. Tool tracker 216 acquires information relation to the position of the tool tip when the tip of tool is in contact or close contact with the eye tissue of interest at one or more points and provides the acquired information to processor 204. Processor 204 determines a model of lens the eye tissue of interest by estimating the geometrical structure and the size thereof, as well as the P&O in a reference coordinate system 218. After procedure 302 the method proceeds to procedure 306. Also, it is noted that procedure 302 is optional.

In procedure 304, the P&O of a tissue reference marker or markers is determined in the reference coordinate system. The P&O of the at least one tissue reference marker is determined, continuously and in real-time according to the acquired image or images thereof. The tissue reference marker may be an anatomical reference marker such as the iris. However, the tissue reference marker or markers may also be the conjunctiva, blood vessels within the conjunctiva or within other organs of the eye. Alternatively, the tissue reference marker or markers may be artificial markers placed on the eye such as a patch attached, fiducial markers or dedicated pen markers drawn on the eye. With reference to FIG. 2, processor 204 determines the P&O of a tissue reference marker in reference coordinate system 218.

In procedure 306, the P&O of the eye tissue of interest is determined in the reference coordinate system. The P&O of the eye tissue of interest is determined, continuously and in real-time, according to P&O of the tissue reference marker or markers and according to the predetermined relative P&O between the tissue reference marker or markers and the eye tissue of interest. Thus, a maneuvering space is determined in which a tool can be maneuvered without causing undesired damage to the tissue (i.e., which may or may not take into account safety distance thresholds). With reference to FIG. 2, processor 204 determines the P&O of the eye tissue of interest. It is noted that procedure 254 is optional.

In procedure 308, the position of at least one tool point of interest is determined in the reference coordinate system. With reference to FIG. 2, tool tracker 216 acquires information relating to the P&O of the tool tip and processor 204 determines the P&O of the tool tip accordingly.

In procedure 310, the distance between the at least one tool point of interest and the eye tissue of interest is determined. With reference to FIG. 2, processor 204 determines the distance between the tool tip and the eye tissue of interest.

In procedure 312, an indication relating to the distance between the tool tip and the eye tissue of interest is produced. This indication may be a visual indication such as a numerical representation of the distance or an array of Light Emitting Diodes, distance bars and the like. As a further example, the visual indication may be presented on a display (e.g., a Liquid Crystal Display—LCD screen, a Heads-Up-Display, a Near-To-Eye display and the like) which shall display the determined 3D model of the eye along with a symbol the tool. The indication may be alternatively or additionally be an audio indication such as a sound with a pitch or volume or both, which varies according to the distance. As a further alternative or in addition, an indication is produced may indicate that the distance between the tool tip and the eye tissue of interest is below a threshold. With reference to FIG. 2, distance indicator 206 produces an indication relating to the distance between the tool tip and the eye tissue of interest.

It will be appreciated by persons skilled in the art that the disclosed technique is not limited to what has been particularly shown and described hereinabove. Rather the scope of the disclosed technique is defined only by the claims, which follow.

The invention claimed is:

1. A system for determining a position of at least one tool point of interest of a tool, relative to an eye tissue of interest, the system comprising:
   an imager configured to acquire images of at least one tissue reference marker;
   a tool tracker configured to acquire information relating to a position and-orientation position and orientation of said tool in a reference coordinate system, said imager and said tool tracker being in registration with said reference coordinate system; and a processor configured to:
determine at least one of position and position and orientation of said at least one tissue reference marker in said reference coordinate system;

determine a position and orientation of said eye tissue of interest in said reference coordinate system based on said at least one of position and position and orientation of said at least one tissue reference marker and a relative position between said at least one tissue reference marker and said eye tissue of interest pre-determined from at least a stored 3-D model of said eye, determine a position of said at least one tool point of interest in said reference coordinate system from said acquired information relating to said position and orientation of said tool in said reference coordinate system, and determine a relative position between said at least one tool point of interest and said eye tissue of interest, based on said determined position and orientation of said eye tissue of interest and said determined position of said at least one tool point of interest.

2. The system according to claim 1 further comprising a distance indicator, coupled with said processor, configured to provide an indication of the distance between said at least one tool point of interest and said eye tissue of interest.

3. The system according to claim 2, wherein said indication of distance is one of a heads up display and a head mounted display.

4. The system according to claim 2, wherein said distance indicator is configured to provide an audio indication that varies according to said distance.

5. The system according to claim 1, wherein said imager is a stereoscopic camera.

6. The system according to claim 1, wherein said imager is a time of flight camera, and said imager further includes a light source configured to emit pulsed light.

7. The system according to claim 1, wherein said imager is a structured light camera, and said imager further includes a light source configured to emit structured light.

8. The system according to claim 1, wherein said at least one tissue reference marker is at least one of:
the iris;
the conjunctiva;
visible blood vessels; and
an artificial marker.

9. The system according to claim 1, wherein said stored 3-D model is acquired by one of Optical Coherence Tomography and ultrasound of the eye.

10. The system according to claim 1, further including a memory coupled with said processor, said memory configured to store said stored 3-D model.

11. The system according to claim 1, wherein said stored 3-D model includes a representation of said at least one tissue reference marker.

12. The system according to claim 1, wherein when said stored 3-D model does not include a representation of said at least one tissue reference marker, said relative position between said stored 3-D model and said at least one tissue reference marker is determined from a measured intra operative model of the eye, said stored 3-D model, and at least one of the position and the position and orientation of said at least one tissue reference marker in said reference coordinate system, wherein said measured intra operative model is determined in said reference coordinate system, wherein said intra operative model and said stored 3-D model include representation of common portions of said eye, and wherein said processor fits said stored 3-D model with said measured intra operative model, thereby determining the position and orientation of said stored 3-D model in said reference coordinate system, and determining at least the position of said stored 3-D model relative to said at least one tissue reference marker, and said relative position between said eye tissue of interest and said at least one tissue reference marker.

13. The system according to claim 12, wherein said measured intra operative model is determined by positioning a tool tip of a modeling tool at a plurality of points on at least part of said common portions of said eye, said tool tracker acquires information relating to the position of a tip position of said modeling tool at each of said plurality of points, said processor estimates a measured intra operative model of said common portions of said eye from the positions of said modeling tool tip at each of said plurality of points in said reference coordinate system.

14. The system according to claim 1 wherein said at least one tool point of interest is a tool tip.

15. A method for determining a position of at least one tool point of interest relative to an eye tissue of interest, the method comprising:
acquiring images of at least one tissue reference marker;
acquiring information relating to a position and orientation of said tool in a reference coordinate system;
determining at least one of position and position and orientation position and orientation of said at least one tissue reference marker in said reference coordinate system;
determining a position and orientation of said eye tissue of interest in said reference coordinate system based on said at least one of position and position and orientation of said at least one tissue reference marker and a relative position between said at least one tissue reference marker and said eye tissue of interest pre-determined from at least a stored 3-D model of said eye;
determining a position of said at least one tool point of interest in said reference coordinate system from said acquired information relating to said position and orientation of said tool in said reference coordinate system;
determining a relative position between said at least one tool point of interest and said eye tissue of interest, based on said determined position and orientation of said eye tissue of interest and said determined position of said at least one tool point of interest.

16. The method according to claim 15, further comprising providing an indication of the distance between said at least one tool point of interest and said eye tissue of interest.

17. The system according to claim 15, wherein said stored 3-D model is acquired by one of Optical Coherence Tomography and ultrasound of the eye.

18. The method according to claim 15, wherein said images are one of stereoscopic images, time of flight images and a-structured light images.

19. The method according to claim 15, wherein said at least one tissue reference marker is at least one of:
the iris;
the conjunctiva;
visible blood vessels; and
an artificial marker.

20. The method according to claim 15, wherein said at least one tool point of interest is a tool tip.

21. The method according to claim 15, wherein said stored 3-D model includes a representation of said at least one tissue reference marker.

22. The method according to claim 15, wherein when said stored 3-D model does not include a representation of said at least one tissue reference marker, a relative position between said stored 3-D model and said at least one tissue reference marker is determined from a measured intra operative model of the eye, said stored 3-D model, and at least one of the position and the position and orientation of said at least one tissue reference marker in said reference coordinate system,
  wherein said measured intra operative model is determined in said reference coordinate system,
  wherein said intra operative model and said stored 3-D model include representation of common portions of said eye, and
  wherein said stored 3-D model is fitted with said measured intra operative model, thereby determining the position and orientation of said stored 3-D model in said reference coordinate system, and determining at least the position of said stored 3-D model relative to said at least one tissue reference marker, and said relative position between said eye tissue of interest said at least one tissue reference marker.

23. The method according to claim 22, wherein said measured intra operative model is determined by:
  positioning a tip of a modeling tool at a plurality of points on the eye tissue;
  acquiring information relating to the position and orientation of said tool marker at each of a plurality of points; and
  estimating a measured intra operative model of the eye tissue from the positions of said tool tip at each of said plurality of points.

* * * * *